United States Patent [19]
Hollingshead et al.

[11] 4,119,791
[45] Oct. 10, 1978

[54] AQUEOUS RECOVERY OF HYDROQUINONE

[75] Inventors: William Shepherd Hollingshead, Cuyahoga Falls; Edward Norbert Nowak, Uniontown, both of Ohio

[73] Assignee: The Goodyear Tire & Rubber Company, Akron, Ohio

[21] Appl. No.: 833,204

[22] Filed: Sep. 14, 1977

[51] Int. Cl.² .................................. C07C 39/08
[52] U.S. Cl. .................................. 568/768; 568/753
[58] Field of Search .......... 260/621 A, 621 R, 625, 260/621 C, 621 H

[56] References Cited

U.S. PATENT DOCUMENTS

| | | | |
|---|---|---|---|
| 3,798,277 | 3/1974 | Sugiyama et al. | 260/621 C |
| 3,884,983 | 5/1975 | Burkholder et al. | 260/621 A |
| 3,895,079 | 7/1975 | Anderson et al. | 260/621 A |
| 3,900,523 | 8/1975 | Tada | 260/621 A |
| 3,968,171 | 7/1976 | Burkholder et al. | 260/621 C |
| 4,049,723 | 9/1977 | Tanaka et al. | 260/621 A |

Primary Examiner—James O. Thomas, Jr.
Assistant Examiner—Werren B. Lone
Attorney, Agent, or Firm—D. B. Little

[57] ABSTRACT

Hydroquinone having a purity greater than 99 percent is isolated through an aqueous recovery scheme compatible with the methyl isobutyl ketone based diisopropylbenzene dihydroperoxide isolation process. Hydroquinone, from the Hock-splitting reaction, is extracted into water while the impurities are concentrated in a distillation tower. Phase separation of the distillation tower bottoms affords an efficient separation of the hydroquinone from the organic impurities. Concentration, crystallization, and solid liquid separation (centrifugation) of the aqueous phase yields a wet hydroquinone cake which, upon recrystallization from acetone, yields high purity hydroquinone.

8 Claims, 1 Drawing Figure

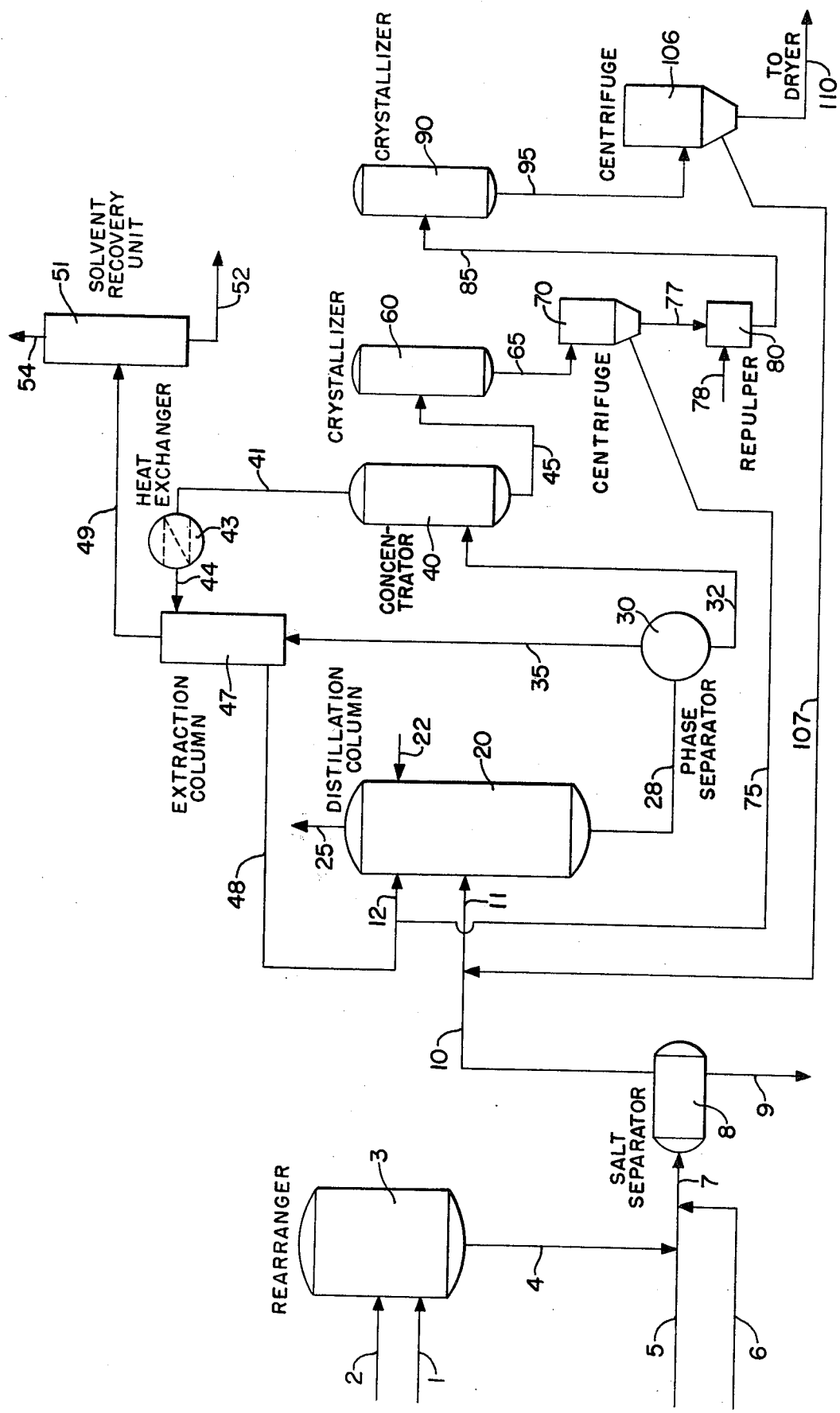

AQUEOUS RECOVERY OF HYDROQUINONE

BACKGROUND OF THE INVENTION

The field of this invention is the synthesis of hydroquinone by acid cleavage (Hock-splitting) and recovery of hydroquinone from the reactor effluent.

The acid catalyzed cleavage or rearrangement of isopropylbenzene hydroperoxide was shown by Hock and Lang, Ber. 77B, p. 257 (1944), thus the name Hock-splitting. This reaction has been developed and used in the manufacture of phenolic compounds, including hydroquinone by the cleavage of p-diisopropylbenzene dihydroperoxide.

There has been a continuing effort on the part of those working in the field to develop a process which has a high level of product purity. The reason for this is that hydroquinone must be a white crystal or crystalline powder which meets ASA specification PH 4.126–1962 in order to be photographic grade. A high standard for whiteness is imperative for photographic grade material. Hydroquinone is used widely as the main ingredient in black and white film print developing.

Hydroquinone is also useful as a polymerization inhibitor and as an antioxidant. Hydroquinone itself and derivatives, such as 2,5-di-tert.-butylhydroquinone and butylated hydroxyanisole (BHA), are used for the prevention of oxidation in animal fat and aviation fuels.

By-products of the Hock-splitting (or rearrangement) reaction, referred to as tars, are believed to be the major impediment to high purity. Among the components of these tars are: p-isopropylphenol, α-hydroxy-p-isopropylphenol, p-diisopropylbenzene, p-isopropenylphenol, isopropenyl acetophenone, and dimers and trimers of the product and by-products. These impurities and by-products must be removed from the rearrangement product mixture in order to obtain a good color grade and high purity product.

Two processes applying the Hock-splitting reaction to p-diisopropylbenzene dihydroperoxide are found in the U.S. Pat. Nos. 3,884,983 and 3,968,171. These processes both employ benzene as a reaction solvent and as an extractant in removing tars.

Benzene has been the subject of recent regulatory action. The Occupational Safety and Health Administration has recently promulgated an emergency temporary standard bringing the average allowed exposure of a worker to benzene down to one part per million on a time-weighted basis, and allowing no more than five parts per million (ppm) peak exposure in factories during any 15-minute period. Even prior to this regulation the exposure was limited to 10 ppm. Thus, it is desirable to limit as much as possible the use of benzene in the process for making hydroquinone.

There are several processes, besides the two already mentioned, which use as the first five unit operations: rearrangement reaction, neutralization, removal of salts from the mixture, distillation and extraction to remove tars. In both Japanese Pat. Nos. 017762 and 18836, the extractant is an aromatic hydrocarbon such as benzene or toluene. U.S. Pat. No. 3,798,277 and Japanese Pat. No. 18835 are similar processes except that their respective extractants are halogenated hydrocarbons such as methylene chloride and alkyl ethers such as isopropylether, both of which are hazardous types of materials.

A significant advance in the processing technology for phenolic compounds occurred when the process for isolating mono and dihydroperoxides by selective extraction first into a caustic solution, then into a water-insoluble organic liquid (exemplified by methyl isobutyl ketone) extractant was developed. This process has been described in Graham, World Petroleum Congress, proceedings, 7th, 1967 (Pub 1968), 5, 29–40 (Great Britain) and in U.S. Pat. Nos. 2,856,432; 2,856,433; 3,190,923; and 3,190,924. This process can be applied to the manufacture of p-diisopropylbenzene dihydroperoxide and insures that this material will enter the rearrangement reactor free of any benzene in the reaction solvent. It has the added benefit of a generally purer feed to the rearrangement reaction.

An application of the above methyl isobutyl ketone (MIBK) process to the manufacture of hydroquinone is described in Ewers, Voges, and Maleck, Erdoel Kohle Erdgas Petrochem, Br. Chem., 28(1) 34+(1975, West Germany). In this process (hereinafter referred to by the name of the owner, Veba-Chemie) A.G. the MIBK extract containing p-diisopropylbenzene dihydroperoxide is distillatively dried and then subjected to the Hock-splitting reaction. Reactor effluent is subjected to neutralization, distillation to remove the acetone formed in the reaction and part of the MIBK reaction solvent, extraction of the distillation bottoms with water, extraction of the hydroquinone-bearing aqueous extract with MIBK to remove impurities, concentration of the purified aqueous extract, and crystallization of the hydroquinone. Parts of this process are described in German Offenlegungsschrift No. 2446992, Apr. 15, 1976.

A process for purifying hydroquinone by successive aqueous extractions of the tars is described in U.S. Pat. No. 3,900,523. In that process it is a steam distillation following the rearrangement reaction which removes the reaction solvent and forms a crude hydroquinone aqueous solution consisting essentially of water, hydroquinone, solvent and tar substances. The concentration of hydroquinone in this aqueous solution must be about 23 weight percent or more at a temperature of about 60° C.

The further purification of hydroquinone by recrystallization from acetone is described in Japanese Pat. Nos. 51039636 and 4872140, and German Offen. No. 2,541,489. In the German and the last mentioned Japanese documents the recrystallization is mentioned in connection with the MIBK process.

A process combining the steps of rearrangement in an MIBK solvent followed by distillation and extraction steps to remove tars and recrystallization of the hydroquinone from acetone has great promise because it eliminates the use of benzene and other hazardous organic liquids as both a solvent and extractant and results in a product of very high purity. One drawback to such a process is the great number of unit operations which must be performed. This invention combines the desirable features of the process just described and, in addition, reduces the number of steps required.

SUMMARY OF THE INVENTION

Hydroquinone may be synthesized by the process steps of:

(A) reacting a feed stream comprising p-diisopropylbenzene dihydroperoxide in a reaction solvent with an acid to form hydroquinone and acetone;

(B) adjusting the pH of the mixture after the reaction by adding a base, thereby causing salts to form and precipitate;

(C) separating the precipitated salts from the supernatant mixture;

(D) distilling the supernatant mixture to remove most of the reaction solvent in the distillate and taking a hydroquinone-containing stream as the bottoms;

(E) subjecting the bottoms to a phase separation wherein the lower aqueous phase contains most of the hydroquinone and the upper organic phase contains substantially all the impurities and a small quantity of hydroquinone;

(F) concentrating the aqueous phase from step (E);

(G) crystallizing hydroquinone from the concentrated stream from step (F);

(H) separating the crystals from step (G) from the supernatant aqueous liquid which is recycled to the distillation step (D);

(I) repulping the crystals in acetone;

(J) crystallizing the hydroquinone from the acetone; and (K) separating the hydroquinone crystals from the supernatant acetone which is recycled to the distillation column (D).

A description of the rearrangement reaction can be found in U.S. Pat. No. 3,968,171, column 3, lines 31–44, which is hereby incorporated by reference into this application. For purposes of this process, the acid catalyst may be present in the range from 0.05 to 3.0 weight percent of the reaction mixture. Water adversely affects the reaction by reducing acid strength and must be below 3 weight percent, preferably below one weight percent. The preferred temperature of the reaction is from 65° to 85° C.

The reaction solvent may be any water-insoluble organic liquid suitable for the selective extraction process (described in the Background section) for isolating p-diisopropylbenzene dihydroperoxide. Thus the extract from the dihydroperoxide process is the feed to the hydroquinone synthesis process. Examples of suitable solvents are: methyl isopropyl ketone, diisopropyl ketone, methyl isobutyl ketone, cyclohexanone, 1-pentanol, 3-pentanol, diethyl ether, diisopropyl ether, ethyl isopropyl ether, and mixtures of the foregoing with acetone.

The pH of the reaction effluent is adjusted to from about 2.5 to 5.5, preferably within the range of 3 to 4. Anhydrous ammonia gas is particularly effective as a neutralization agent because it is readily dispersible in the organic solution. Other bases which are useful are described in U.S. Pat. No. 3,927,124, column 2, lines 67–68 and column 3, lines 1–9, which is incorporated by reference into this application. That same patent describes a process for the pH adjustment or neutralization at columns 3, lines 15–54 which is also incorporated by reference into this application. The pH adjustment may also be accomplished by simply mixing the base with the rearranger effluent.

The salt of the acid catalyst formed during the neutralization of pH adjustment step is insoluble in the reaction solvent and may thus be removed by precipitation, filtration or any other suitable solid liquid separation step. If precipitation is used, water is added to the reactor effluent prior to the salt separation step to facilitate the separation by dissolution of said salts into an aqueous phase which is withdrawn.

The supernatant liquid or filtrate from the salt separation step flows on to a distillation column in which are combined the unit operations of distillation to remove the acetone and reaction solvent and extraction of the hydroquinone into a water phase. The hydroquinone content of this supernatant stream will generally be from 1 to 15 weight percent, and is preferably from about 5 to 15 weight percent. In addition to the neutralized supernatant mixture, the distillation column feed includes two other streams, an acetone stream and an aqueous stream, both of which may contain impurities and minor constituents not critical to the present process.

The amount of water fed to the distillation column should be sufficient to both insure the transfer of most of the hydroquinone to the aqueous phase and to compensate for water lost in the overhead with any reaction solvent/water azeotrope.

The ratio of organic to aqueous phase in the distillation bottoms is critical and depends on how pure the p-diisopropylbenzene dihydroperoxide feed is. The purer the feed is the smaller may be the ratio because the organic phase would have to "hold" less tars. Generally the weight ratio is between 0.5:10 and 5:10 and preferably is about 1:10. A ratio of 1:10 gives a good balance between the goals of minimizing the flow of organic phase in the bottoms and allowing some flexibility in the operation of the distillation column. In experiments an organic to aqueous phase volume ratio of about 1/10 in the distillation tower bottoms resulted in the transfer of 88 weight percent of the hydroquinone to the aqueous phase. The solubility of tars in water is negligible.

The acetone feed along with the acetone obtained as a product of the rearrangement reaction is removed by distillation as overhead. The overhead also includes most of the reaction solvent (e.g. MIBK). In the case of MIBK, since the distribution coefficient for hydroquinone in the MIBK/$H_2O$ system favors MIBK by a factor of 3 to 5, the volume of the MIBK phase in the bottoms has to be reduced by distillation sufficiently to counter this unfavorable situation.

The tower bottoms stream comprises an organic phase comprising reaction solvent in which are dissolved the tars and some hydroquinone and a water phase in which is dissolved most of the hydroquinone. The concentration of hydroquinone in this aqueous phase is about 5 to 25 weight percent, preferably 8 to 10 weight percent.

The concentration step (F) is generally run at a temperature from 65° to 100° C., preferably from 65° to 75° C. The aqueous phase is usually concentrated to from 25 to 30 weight percent hydroquinone. Lower concentrations tend to reduce crystallization yields, and higher concentrations tend to give a slurry which is too viscous.

The term "repulping" as used herein means dissolving a wet precipitate such as a filter cake or centrifuge cake in a solvent. The concentration of hydroquinone in the mixture leaving step (I) is generally between 30 and 50 weight percent. The purer the cake is, the higher the concentration can be.

For obvious reasons of economy it is desirable to treat the tar-containing organic phase from the phase separation step (E) to separate therefrom the hydroquinone which it contains and which might otherwise be destroyed in a subsequent tar removal step. The following steps may be added in order to accomplish this separation:

(L) cooling the overhead aqueous vapor from step (F);

(M) extracting the organic phase from step (E) countercurrently with the cooled aqueous stream from step (L) under such conditions that most of the hydroquinone is transferred into the aqueous extract phase and most of the impurities remain in the organic raffinate phase;

(N) transferring the aqueous extract to the distillation step (D);

(O) recovering from the organic raffinate of step (M) substantially all of the reaction solvent.

The conditions necessary for step (M) are a volume flow of water extractant that is several times that of the organic feed (e.g. 7:1) and an extraction temperature of about 80° C. Temperatures of up to 120° C. are permissible if pressure is employed in the extraction.

The function of the solvent recovery step (O) is to purify the tar-containing raffinate from step (M) so that it may be recycled back into the process. This purification may be done by any suitable unit operation such as distillation or evaporation.

The process with the addition of these four purification steps has the advantage that more hydroquinone is obtained as a useful product. Also, the water evaporated in concentration step (F) is utilized as an extractant in step (M) and is recycled to step (D) thus greatly reducing the water consumption which would otherwise be necessary.

The fact that the organic phase from the phase separator which is water extracted is a relatively small volume compared to the total tower bottoms flow (which is extracted in the Veba-Chemie process) allows the equipment for handling this stream to be much smaller.

DESCRIPTION OF THE DRAWING

The single FIGURE is a diagrammatic representation of the process of the present invention.

DESCRIPTION OF THE PREFERRED EMBODIMENTS

As an aid in understanding the process of this invention, the overall process will be described with reference to the flow diagram, with the proviso that this diagram is an exemplary embodiment of the invention and the process is not limited to this particular arrangement. For example, the solid liquid separation step (H) is shown as a centrifuge; however, this operation could be done by a filter. The symbols represent unit operations, and ancillary equipment such as heat exchangers, pumps, and steam jet ejectors have not been illustrated. Also, secondary process streams (e.g. vapor leaving crystallizers) and utility streams (e.g. steam) have been omitted.

Referring to the drawing, the rearranger feed 1 contains p-diisopropylbenzene dihydroperoxide, reaction solvent and minor amounts of unreacted p-diisopropylbenzene (precursor to the dihydroperoxide) and impurities such as diisopropylbezene monohydroperoxide and α-hydroxy-α'-hydroperoxy diisopropylbenzene. This feed is mixed in the rearranger reactor 3 with the acid catalyst 2 (such as sulfuric acid). Typical conditions for the rearrangement reaction are 180° F. (82° C.) and 0 to 20 pounds per square inch gauge pressure (0 – 138 kilopascals).

The rearranger effluent 4 is mixed in-line with anhydrous ammonia gas which enters via stream 5 and water which enters via stream 6. The acid present in the reactor effluent is neutralized and this neutralized stream 7 enters the salt separator 8.

The salt separator 8 consists of a vessel designed so that it has sufficient holding capacity to permit the transfer of the acid salts to the aqueous phase 9 and the removal of the supernatant organic stream 10 without disturbing this transfer.

Stream 10 is mixed with the acetone filtrate 107 from centrifuge 106 and the combined stream 11 flows onto the distillation column 20. To the distillation column is also fed an aqueous stream 12 which consists of a combination of the aqueous extract 48 from extraction column 47 and filtrate stream 75 from centrifuge 70. Any deficiency in the amount of water necessary is made up by adding water via stream 22. The distillation is carried out, as described in the summary section, so as to remove all of the acetone and most of the reaction solvent in the distillate 25. At the same time the hydroquinone is extracted into the aqueous phase and tars are concentrated in the organic phase in the distillation bottoms 28.

The two-phase bottoms stream 28 flows on to phase separator 30, which is a vessel designed to permit the decantation of the organic phase from the aqueous phase which contains the hydroquinone. The aqueous phase 32 is withdrawn and transferred to concentrator 40.

The concentrator 40 is typically operated under a vacuum (e.g. 540 mm. Hg absolute) and at an elevated temperature (e.g. 66° C.). The function of the concentrator is to remove sufficient water in order to successfully carry out the next unit operation, crystallization. The water removed leaves the concentrator via stream 41. The concentrate exits the concentrator via stream 45.

In the crystallizer 60, crystals of hydroquinone are formed through gentle cooling and agitation, forming an aqueous slurry. This slurry 65 may be removed on a continuous or batchwise basis from the crystallizer.

Stream 65 flows on to centrifuge 70 in which the wet hydroquinone crystals 77 are separated from the aqueous filtrate 75.

The wet crystals 77 are transferred to repulper 80. The repulper 80 is an agitated vessel in which the wet hydroquinone crystals are dissolved in acetone which enter via stream 78. The mixture of hydroquinone, acetone and water thus formed, 85, flows from the repulper to crystallizer 90.

Crystallizer 90 performs a similar function to crystallizer 60 with the exception that the solvent system is principally acetone instead of water. A slurry of hydroquinone crystals in the acetone solvent 95 exits the crystallizer 90 and flows on to centrifuge 106.

Centrifuge 106 separates the hydroquinone crystals 110 (this time wet with acetone) from the acetone filtrate 107 which is recycled to the distillation column 20. Following centrifugation, the wet hydroquinone crystals are conveyed to a dried for conventional handling thereafter.

The tar-containing organic phase 35 is transferred from phase separator 30 to extraction column 47 where it is contacted countercurrently with aqueous stream 44 (recycled stream 41 condensed in heat exchanger 43). Extraction column 47 is operated, as stated in the summary section, so that most of the hydroquinone in the organic phase is extracted into the aqueous phase. The hydroquinone-containing aqueous extract 48 is recycled to distillation column 20. The tar-containing organic raffinate 49 flows on to solvent recovery unit 51 where it is separated into relatively pure reaction solvent 54 and concentrated tars 52.

A better understanding of the present invention will be obtained from the following working example which is merely illustrative and not limitative of the present invention. Unless otherwise stated, percentages are by weight.

EXAMPLE

A feed mixture was made by combining 230 grams of p-diisopropylbenzene dihydroperoxide (p-DHP) cake with 615 grams of MIBK and 93 grams of acetone and warming to 60° C. The cake was obtained as the product of a process similar to that described in U.S. Pat. No. 3,883,600 (column 7, lines 9–13) and in *Chemical Engineering*, June 9, 1975, pp. 50–51 (vacuum drum filter cake). The cake was comprised of 85.6 percent p-DHP, 12.8 percent $\alpha$-hydroxy-$\alpha'$-hydroperoxy diisopropylbenzene and 1.6 percent p-diisopropylbenzene.

Five milliliters of 50 percent $H_2O_2$ was added to the solution in order to convert any $\alpha$-hydroxy-$\alpha'$-hydroperoxy diisopropylbenzene and $\alpha,\alpha'$-dihydroxydiisopropylbenzene (both of which may be present in the cake) to hydroquinone. This technique is explained in British Pat. No. 910,735. It helps to improve the yield.

The rearrangement was initiated by the addition of this p-DHP feed to a nitrogen-purged three liter flask containing 2 grams of concentrated $H_2SO_4$ in 80 grams of acetone. An additional one gram of concentrated $H_2SO_4$ was added to the reaction flask after one-half of the p-DHP feed has been added. The temperature of the rearrangement was maintained at 65° to 75° C. and was controlled by the adjustment of the rate of the addition of the feed and with external cooling in an ice bath. After all the feed was added, the rearranged solution was allowed to stand with stirring for an additional 10 minutes, neutralized with anhydrous $NH_3$ to a pH of 3.5 to 4.5 and vacuum filtered to remove the salts.

The rearranger effluent was then combined with the recycle streams (48, 75 and 107) from the previous cycle and the resulting mixture was distilled atmospherically to remove the acetone and to concentrate the MIBK containing the impurities to a level at which most of the hydroquinone would be in the aqueous phase. An organic to aqueous phase volume ratio of about 1 to 10 resulted in the transfer of 88 percent of the hydroquinone to the aqueous phase. The addition of water here was necessary to compensate for the water lost overhead in the MIBK/water azeotrope and to assure a hydroquinone concentration of 9 to 10 percent in the aqueous phase of the two phase distillation tower bottoms. After phase separation of the distillation tower bottoms, the hydroquinone remaining in the organic phase (stream 35) was extracted with water at 80° C. The aqueous phase from this extraction (stream 48) was then returned to the succeeding cycle through the distillation tower.

The aqueous layer from the phase separation of the distillation tower bottoms (stream 32) was then concentrated by vacuum distillation to a hydroquinone content of 25 percent, cooled to 25° C. and centrifuged to obtain a wet hydroquinone cake (stream 77). The centrifuge filtrate (stream 75) was recycled to the distillation tower. The hydroquinone cake, which contained about 20 percent water, was combined with an amount of acetone equal in weight to the cake, warmed until in solution, cooled to 20° C., and centrifuged to recover high purity hydroquinone. The centrifuge filtrate (stream 107) was recycled back to the distillation tower.

One measurement of hydroquinone purity is color number. Color number is an arbitrary color measurement obtained by comparing a 5 percent hydroquinone solution in a dilute acetic acid with a known set of color standards. The color standard is a platinum/cobalt (Pt/Co) standard of the American Public Health Association (APHA). A standard color number curve is plotted using various solutions of the standard. As furnished, the standard has a color number of 500. A one percent solution would then have a color number of 5, etc. Measurements of light absorbance are made on an instrument such as Beckman Spectrophotometer at a wave length of 390. For hydroquinone, a color number of less than or equal to 20 corresponds to commercially available photograde hydroquinone and meets the ASA specification for color and acetone solubility.

The procedure described in the experimental section above was worked batchwise through seven cycles to determine the extent of color build-up or the decay of purity of the hydroquinone. The product of the seventh cycle had a purity of 99 percent and a Pt/Co color number of 22. The crude cake before crystallization from acetone had a Pt/Co color number of about 300 and had a needle-like structure with rather poor flow properties characteristic of hydroquinone recovered by crystallization from water.

While certain representative embodiments and details have been shown for the purpose of illustrating the invention, it will be apparent to those skilled in this art that various changes and modifications may be made therein without departing from the spirit or scope of the invention. For example, the solvent recovery step (O), represented by item 51 on the flow diagram, may be eliminated if the organic raffinate (49) can be utilized or properly disposed of.

What is claimed is:

1. In a process for making hydroquinone comprising the steps of:
    (A) reacting a feed stream comprising p-diisopropylbenzene dihydroperoxide
        (1) in a reaction solvent selected from the group consisting of methyl isopropyl ketone, diisopropyl ketone, methyl isobutyl ketone, cyclohexanone, 1-pentanol, 3-pentanol, diethyl ether, diisopropyl ether, ethylisopropyl ether and mixtures of the foregoing with acetone;
        (2) with an acid catalyst selected from the group consisting of $H_3PO_4$, $HClO_4$, p-toluene-sulfonic acid, $SO_2$, $HBF_4$, $H_2SiF_6$, $BF_3$ and any Lewis acid in a concentration of from 0.05 to 3.0 weight percent of the reaction mixture;
        (3) with less than three weight percent water present in the reaction mixture;
        (4) within a temperature range of from 50° to 100° C. to form hydroquinone and acetone;
    (B) adjusting the pH of the mixture to from about 2.5 to 5.5 after the reaction by adding a base selected from the group consisting of anhydrous ammonia, methylamines, triethylamines, and alkali and alkaline earth metal hydroxides, carbonates and oxides, thereby causing salts to form and precipitate; and (C) separating the precipitated salts from the supernatant mixture; the improvement which comprises the steps of:

(D) feeding the supernatant mixture to a distillation column in which are combined the unit operations of distillation, to remove the acetone and most of the reaction solvent in the distillate, and extraction of the hydroquinone into a water phase which exits the distillation column together with an organic phase as the distillation bottoms stream;

(E) subjecting the bottoms to a phase separation wherein the aqueous phase contains most of the hydroquinone and the organic phase contains substantially all the impurities and a small quantity of hydroquinone;

(F) concentrating the aqueous phase from step (E);

(G) crystallizing hydroquinone from the concentrated stream from step (F);

(H) separating the crystals from step (G) from the supernatant aqueous liquid which is recycled to the distillation step (D);

(I) repulping the crystals in acetone;

(J) crystallizing the hydroquinone from the acetone; and (K) separating the hydroquinone crystals from the supernatant acetone which is recycled to the distillation column (D).

2. The process improvement as recited in claim 1 wherein step (C) is a filtration.

3. The process improvement as recited in claim 1 wherein step (C) is a precipitation.

4. The process improvement as recited in claim 1 wherein step (A) is carried out with methyl isobutyl ketone as the reaction solvent, sulfuric acid as the catalyst, at a temperature of from 65° to 85° C., and with less than one weight percent water in the reaction mixture; and wherein the pH is adjusted to from 3 to 4 with anhydrous ammonia in step (B).

5. The process improvement as recited in claim 4 wherein the hydroquinone concentration in the supernatant mixture from step (C) is from 1 to 15 weight percent; the weight ratio of organic phase to aqueous phase in the distillation bottoms is between 0.5:10 and 5:10; and the concentration of hydroquinone in said aqueous phase is from 5 to 25 weight percent.

6. The process improvement according to claim 5 wherein the concentration of hydroquinone from the repulping step (I) is between 30 and 50 weight percent.

7. The process improvement according to claim 6 wherein the hydroquinone concentration in the supernatant mixture from step (C) is from 5 to 15 weight percent; the weight ratio of organic phase to aqueous phase in the distillation bottoms is about 1:10; and the concentration of hydroquinone in said aqueous phase is from about 8 to 10 weight percent.

8. The process improvement of claim 1 further comprising the steps of:

(L) cooling the overhead aqueous vapor from step (F);

(M) extracting the organic phase from step (E) countercurrently with the cooled aqueous stream from step (L) under such conditions that most of the hydroquinone is transferred into the aqueous extract phase and most of the impurities remain in the organic raffinate phase;

(N) transferring the aqueous extract from step (M) to the distillation step (D); and (O) recovering from the organic raffinate of step (M) substantially all of the reaction solvent.

* * * * *

UNITED STATES PATENT AND TRADEMARK OFFICE
CERTIFICATE OF CORRECTION

PATENT NO. : 4,119,791
DATED : Oct. 10, 1978
INVENTOR(S) : William Shepherd Hollingshead It is certified that error appears in the above-identified patent and that said Letters Patent are hereby corrected as shown below:

Column 6, Line 60 - "dried" should be --drier--.

Signed and Sealed this

Tenth Day of November 1981

[SEAL]

Attest:

GERALD J. MOSSINGHOFF

Attesting Officer   Commissioner of Patents and Trademarks